(12) United States Patent
Liu

(10) Patent No.: US 10,478,327 B2
(45) Date of Patent: Nov. 19, 2019

(54) POSTURAL RECOVERY GARMENT DEVICE SYSTEM

(71) Applicant: IFGCure Holdings, LLC, Los Angeles, CA (US)

(72) Inventor: Stephen H. Liu, Los Angeles, CA (US)

(73) Assignee: IFGCURE HOLDINGS, LLC, Los Angeles, CA (US)

( * ) Notice: Subject to any disclaimer, the term of this patent is extended or adjusted under 35 U.S.C. 154(b) by 26 days.

(21) Appl. No.: 16/125,402

(22) Filed: Sep. 7, 2018

(65) Prior Publication Data

US 2019/0254857 A1 Aug. 22, 2019

Related U.S. Application Data

(63) Continuation-in-part of application No. 16/051,155, filed on Jul. 31, 2018, now abandoned, which is a continuation-in-part of application No. 16/024,881, filed on Jul. 1, 2018.

(60) Provisional application No. 62/672,932, filed on May 17, 2018, provisional application No. 62/633,962, filed on Feb. 22, 2018, provisional application No. 62/637,138, filed on Mar. 1, 2018.

(51) Int. Cl.
*A61F 5/00* (2006.01)
*A61F 5/02* (2006.01)
*A41B 1/08* (2006.01)

(52) U.S. Cl.
CPC .............. *A61F 5/026* (2013.01); *A41B 1/08* (2013.01); *A41B 2300/22* (2013.01); *A41B 2400/22* (2013.01); *A41B 2400/32* (2013.01); *A41B 2500/50* (2013.01)

(58) Field of Classification Search
CPC ........ A41B 2300/22; A41B 1/08; A61F 5/026
See application file for complete search history.

(56) References Cited

U.S. PATENT DOCUMENTS 2,575,700 A * 11/1951 Artzt .................. A41B 9/06
2/113
2,591,462 A 4/1952 Mungo
(Continued)

FOREIGN PATENT DOCUMENTS

CN 2922842 7/2007
CN 201048997 4/2008
(Continued)

OTHER PUBLICATIONS

International Search Report PCT/US2018/040527 Completed Oct. 12, 2018; dated Oct. 23, 2018 4 pages.
(Continued)

*Primary Examiner* — Richale L Quinn
(74) *Attorney, Agent, or Firm* — Ferguson Case Orr Paterson LLP

(57) ABSTRACT

A wearable garment device, design, and method of manufacture that to support proprioceptive posture recovery and rebalance. The wearable device can be stand alone or integrated as lining into any outer apparel for daily wear with the additional therapeutic posture correction. The wearable device maintains breathability, comfort for daily wear, improves function, range of motion, and aesthetic appeal. A wear tech garment device and method of manufacture.

8 Claims, 10 Drawing Sheets

(56) References Cited

U.S. PATENT DOCUMENTS

| | | | |
|---|---|---|---|
| 3,116,735 A * | 1/1964 | Geimer | A61F 5/026 128/DIG. 19 |
| 3,856,004 A * | 12/1974 | Cox | A61F 5/05808 128/DIG. 19 |
| 4,202,327 A | 5/1980 | Glancy | |
| 4,957,103 A | 9/1990 | Young et al. | |
| 5,158,531 A | 10/1992 | Zamosky | |
| 5,451,200 A | 9/1995 | LaBella et al. | |
| 5,599,286 A | 2/1997 | Labelle et al. | |
| 5,718,670 A | 2/1998 | Bremer | |
| 6,102,897 A | 8/2000 | Christensen et al. | |
| 6,213,922 B1 | 4/2001 | Afanasenko et al. | |
| 6,440,094 B1 | 8/2002 | Maas | |
| 6,676,617 B1 | 1/2004 | Miller | |
| 6,936,021 B1 | 8/2005 | Smith | |
| 7,134,969 B2 | 11/2006 | Citron et al. | |
| 7,153,246 B2 | 12/2006 | Koscielny et al. | |
| 7,395,557 B1 | 7/2008 | Ledyard | |
| 7,662,121 B2 | 2/2010 | Zours | |
| 7,871,388 B2 | 1/2011 | Brown | |
| 8,047,893 B2 | 11/2011 | Fenske | |
| 8,083,693 B1 * | 12/2011 | McKeon | A61B 5/103 600/587 |
| 8,308,670 B2 | 11/2012 | Sandifer et al. | |
| 8,516,614 B2 | 8/2013 | Karasina | |
| 8,795,213 B2 | 8/2014 | Mills | |
| 8,795,215 B2 | 8/2014 | Rossi | |
| 8,887,315 B2 | 11/2014 | Boynton | |
| 8,905,956 B2 | 12/2014 | Waeger | |
| 8,910,317 B2 | 12/2014 | Decker | |
| 8,932,236 B1 | 1/2015 | McKeon et al. | |
| 9,009,863 B2 | 4/2015 | Decker | |
| 9,167,854 B2 | 10/2015 | Levian | |
| 9,168,167 B2 | 10/2015 | Brown | |
| 9,226,534 B2 | 1/2016 | Puni | |
| 9,439,459 B2 | 9/2016 | Placanica et al. | |
| 9,445,932 B2 | 9/2016 | Boynton | |
| 9,456,919 B2 | 10/2016 | Pollack | |
| 9,504,280 B2 | 11/2016 | Levian | |
| 9,883,703 B2 | 2/2018 | Schultz | |
| 9,931,236 B2 | 4/2018 | Williamson et al. | |
| 2004/0107479 A1 | 6/2004 | Dicker et al. | |
| 2005/0197607 A1 * | 9/2005 | Brown | A61F 5/026 602/19 |
| 2006/0000478 A1 | 1/2006 | Taylor | |
| 2007/0271671 A1 * | 11/2007 | Okajima | A41D 1/04 2/69 |
| 2008/0134409 A1 | 6/2008 | Karasina | |
| 2008/0295230 A1 * | 12/2008 | Wright | A41D 13/0015 2/455 |
| 2009/0062704 A1 * | 3/2009 | Brown | A41D 13/0015 602/19 |
| 2010/0192274 A1 | 8/2010 | Karasina | |
| 2011/0131697 A1 | 6/2011 | Kawahara | |
| 2012/0078149 A1 | 3/2012 | Azimzadeh | |
| 2012/0174282 A1 | 7/2012 | Newton et al. | |
| 2013/0047313 A1 | 2/2013 | Windisch et al. | |
| 2013/0053744 A1 | 2/2013 | Convert et al. | |
| 2013/0090521 A1 | 4/2013 | Lau et al. | |
| 2013/0103079 A1 | 4/2013 | Lau et al. | |
| 2013/0104280 A1 * | 5/2013 | Boynton | A61F 5/026 2/79 |
| 2014/0058307 A1 | 2/2014 | Marshall | |
| 2014/0100501 A1 | 4/2014 | Burke et al. | |
| 2014/0174454 A1 * | 6/2014 | Naef | A61F 5/3723 128/845 |
| 2014/0221893 A1 | 8/2014 | Modglin | |
| 2014/0336556 A1 * | 11/2014 | Pucik | A61F 5/02 602/19 |
| 2015/0040286 A1 * | 2/2015 | Schultz | A41D 1/00 2/88 |
| 2015/0148727 A1 * | 5/2015 | Collier | A61F 5/026 602/19 |
| 2016/0015090 A1 | 1/2016 | Mazourik et al. | |
| 2016/0278963 A1 * | 9/2016 | Webster | A61F 5/026 |
| 2017/0143048 A1 | 5/2017 | Bucciarelli, III | |
| 2017/0160058 A1 * | 6/2017 | Limpisvasti | A41D 13/00 |
| 2017/0216077 A1 * | 8/2017 | Chahrour | A61F 5/026 |
| 2017/0231798 A1 * | 8/2017 | Shin | A61F 5/02 2/44 |
| 2018/0132543 A1 | 5/2018 | Schultz | |
| 2018/0153727 A1 * | 6/2018 | Hecht | A61F 5/026 |
| 2018/0317562 A1 * | 11/2018 | Gagliardo | A41B 1/08 |
| 2018/0325714 A1 * | 11/2018 | Froula | A61F 5/026 |

FOREIGN PATENT DOCUMENTS

| | | |
|---|---|---|
| CN | 201048998 | 4/2008 |
| CN | 201048999 | 4/2008 |
| CN | 201049000 | 4/2008 |
| CN | 201049001 | 4/2008 |
| CN | 201049002 | 4/2008 |
| CN | 201160505 | 12/2008 |
| CN | 201316333 | 9/2009 |
| EP | 3315103 | 5/2018 |
| JP | 56-104517 | 8/1981 |
| JP | 62-160924 | 10/1987 |
| JP | 2007119994 | 5/2007 |
| JP | 2008279065 | 11/2008 |
| JP | 2011072323 | 4/2011 |
| JP | 2013112912 | 6/2013 |
| KR | 20140005824 | 11/2014 |
| WO | 9635400 | 11/1996 |

OTHER PUBLICATIONS

Written Opinion of the International Searching Authority PCT/US2018/040527 dated Oct. 23, 2018 12 pages.

* cited by examiner

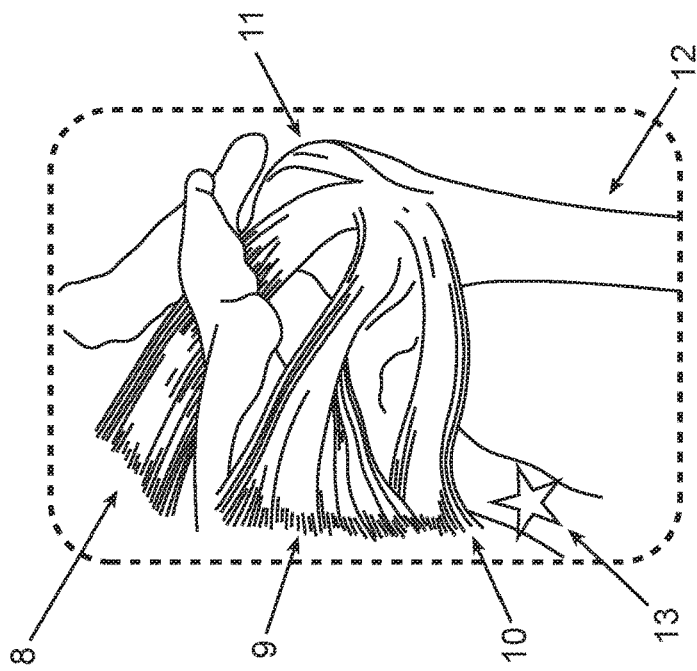
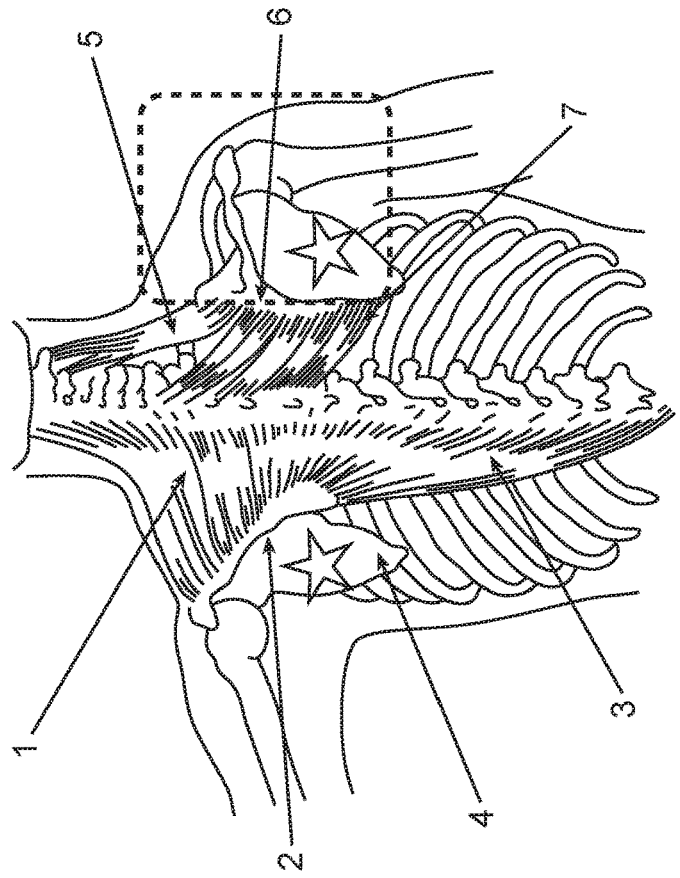
FIG. 6A
FIG. 6B

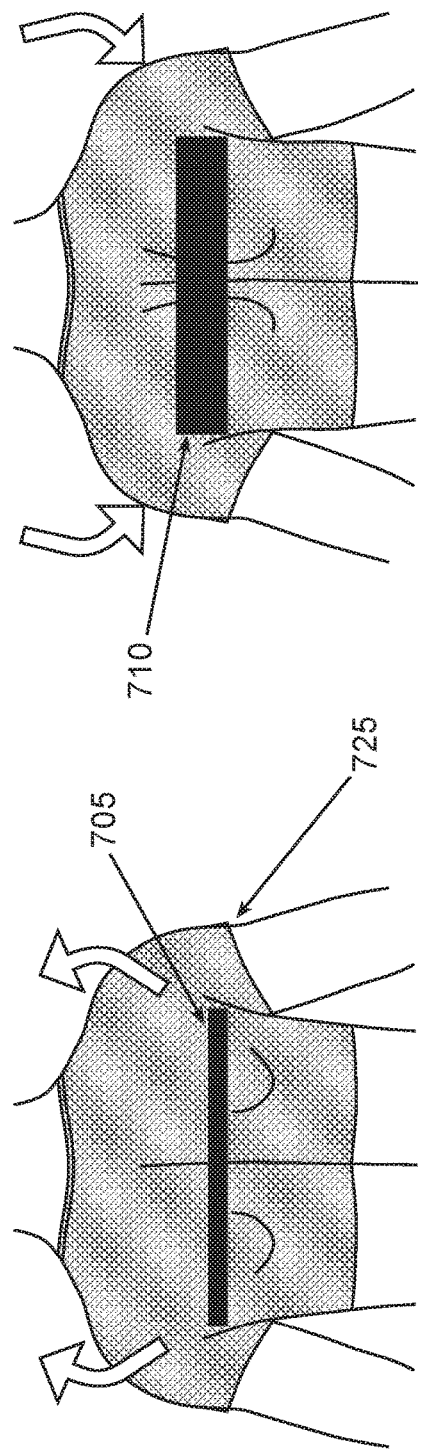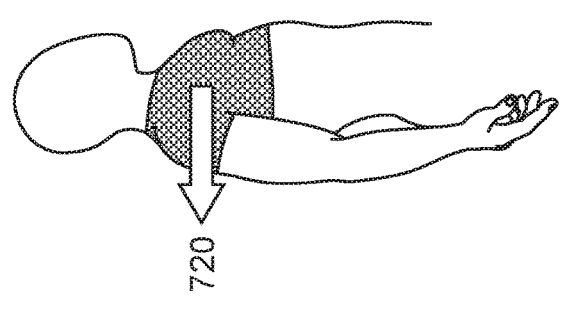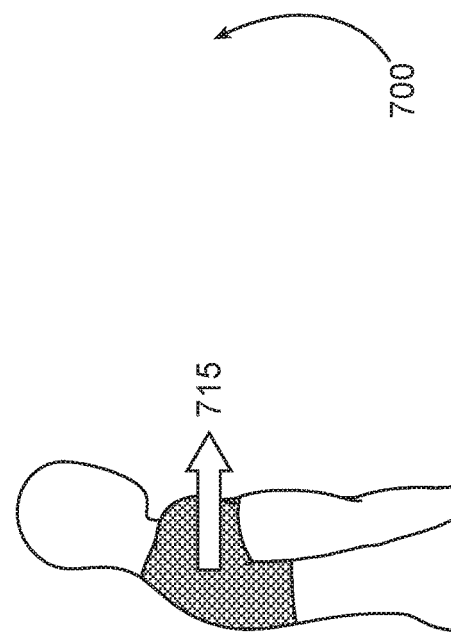
FIG. 7A
FIG. 7B

POSTURAL RECOVERY GARMENT DEVICE SYSTEM

CROSS-REFERENCE TO RELATED APPLICATIONS

This application is a continuation-in-part application of U.S. patent application Ser. No. 16/051,155 entitled POSTURE, PERFORMANCE, RECOVERY GARMENT DEVICE SYSTEM filed on Jul. 31, 2018, which is a continuation-in-part application of U.S. patent application Ser. No. 16/024,881 entitled POSTURE, PERFORMANCE, RECOVERY GARMENT DEVICE SYSTEM filed Jul. 1, 2018, which claim the benefit of priority of U.S. Provisional Application No. 62/672,932 entitled POWER, POSTURE, RECOVERY GARMENT DEVICE SYSTEM, filed May 17, 2018. The contents of all applications are hereby incorporated by reference herein in their entirety.

FIELD OF THE INVENTION

The present invention is a wearable technology garment device (method of design and manufacture) that is configured to be sewn or integrated into any garment for aesthetic appeal, comfort, and maintain therapeutic function. The present invention is directed to a wearable garment device, design, function, and method of manufacture in the posture correction, muscle re-balance, occupation injury risk prevention, and athletic performance, rehabilitation enhancement space. The present invention is directed to a wearable technology garment device, design, function, and method of manufacture that supports and enhances proprioceptive posture rebalance, correct slouching, athletic enhancement and maintains posture alignment, function, and aesthetic appeal.

BACKGROUND OF THE INVENTION

Posture correcting shirts have existed and have been used for several years, the primary goal being to stimulate the body's joints and muscles into better alignment and posture (a slight S-shape of the spine being the gold standard). The importance of having good posture is a well-known and accepted idea among health professionals and non-experts in the field. Good posture helps for both maintaining regular health (back, shoulder, neck pain, etc.) and improving athletic performance, as poor posture during dynamic activities results in inefficient biomechanics and body movement. Indeed, a disruption at any point during the kinetic chain of movement can affect downstream functions as well. Poor posture in the upper body is typically categorized by 'shoulders rolled forward', 'a forward curvature in the thoracic spine', and/or a 'left/right lean of the thoracic spine'. In addition, the inefficient body movement created by poor posture does not allow for full utilization of muscular range of motion and strength and can cause repetitive injury over time.

Typical recovery methods for those suffering from back, neck, and other pain include going to a chiropractor or physical therapy or to seek orthopedic surgeon evaluation. Such medical procedures to correct poor posture involve injections, medications, rehabilitation, and possible surgical correction. As many people cannot afford the time or cost of extensive and costly chiropractor treatments (either short term or long-term treatments), there exists a need in the market for affordable methods and systems to correct and maintain the posture of individuals in attempt to provide:

a) correct functional anatomy;
b) improved muscle efficiency;
c) improved pain relief and minimal pain to users; and
d) creation of good habits so that individuals do not develop poor-posture related pain to begin with.

The first attempts using a wearable garment to refine biomechanical factors that influence posture and kinesthetic states was originated in the 1970's within the Soviet space program, in order to counteract the effects of long-term weightlessness. This device, known as the Adeli suit, is used to treat pediatric patients with postural disabilities due to neurological conditions that lead to brain damage or spinal cord injury. Its design is relatively simple, involving elastic connections between the primary joints, specifically to target positions of antagonistic muscle pairs. However, there are still many other ways and degrees to which the body can become imbalanced due to disruptions in the kinetic chain of muscle activation.

Muscles devoted substantially to the concepts of balance and posture are sometimes referred to as gravity and antigravity muscles; they are the tools that provide upright organisms with the ability to maintain the center-of-gravity (COG) within a stable base of support. Upright balance is attained when a vertical line follows from the center-of-gravity, directly down through this base of support. Any imbalance will cause compensatory abnormalities which will affect alignment within the body's whole musculoskeletal system. Optimized postural alignment is crucial in counteracting the constant downward gravitational forces opposing the body. When the upright force of musculoskeletal architecture and the downward force of gravity are balanced, muscles are able to function with the least amount of work, i.e. peak efficiency.

When the upright body holds better posture, smaller amounts of stress and strain are placed on the muscles, ligaments and bones thereby enhancing their efficiency and increasing bone density and muscle mass in the long term. Opposing the force of gravity, the so called antigravity muscles assist to maintain an upright, balanced posture. For the lower body, these muscles consist of namely the soleus muscles, the extensors of the leg, the gluteus maximus, the quadriceps femoris. For the upper body and the muscles of the back, these muscles include the trapezius, the rhomboids, and several smaller groups around the shoulder such as the teres minor and subscapularis. Additionally, the cervico-occipital muscle groups maintain the head in an erect position, thereby preventing it from rolling forward. These muscle groups simultaneously play an important role in the proprioception process, with proprioceptors in the dermal surface sending key information about pressure in the feet to the antigravity muscles through the nervous system. Any weakening of these muscles combined with the continuously working gravitational forces leads to poor postural stability, which affects muscle function. If left untreated, this ultimately leads to degeneration of joints and deformities such as a structural collapse in the foot. Postural alignment is essential to maintain normal length-tension relationships of the muscles especially during dynamic posture, determining the ease with which the body segments align themselves throughout movement. Any disruptions to this alignment throws the kinetic chain of the body off balance, making the person susceptible to a host of injuries. Understanding our limitations at controlling the effect gravitational forces have on the muscles and structure should form the basis of treatment programs.

As one treatment option, posture shirts and girdles were created to fill the burgeoning need of postural correction.

Posture shirts and girdles typically contain vertical straps that do not mimic natural anatomical movement. These vertical straps take the wrong approach to correcting a wearer's posture, namely that the straps do not focus on proprioceptive correction to achieve natural postural alignment but instead focus on force. This force creates an unnatural alignment that may push a wearer's shoulders backwards in an outward appearance of better posture but in reality, doesn't achieve much short term or long-term success. Natural posture alignment in the thoracic spine is achieved when posterior muscle groups (i.e. trapezius, rhomboids, latissimus dorsi) and anterior muscle groups (serratus anterior, etc.) are both exerting the same amount of force, thus allowing the body to be balanced. Therefore, garments created in this space targeted this natural (proprioceptive) balancing; however, these garments were not able to fully achieve this goal due to several limitations, including the one listed above.

Further to this idea, the vertical straps that these companies utilize end at the bottom of the buttocks, contributing to the unnatural pull that forces the shoulders back into an improper and unnatural position that does not mimic natural anatomical movement. The corresponding picture would be someone grabbing the bottom of one's shirt from the back and pulling it downwards and tucking it underneath one's glutes; this would certainly force one's shoulders back and posture to be straightened but it would also align the posture in the incorrect form and prove to be extremely uncomfortable. For instance, one shirt of this kind was made from a cotton body with elastic straps that were attached at the front of each shoulder, ran over the back parallel to the spine, and connected at the bottom seam. That same shirt was not only anatomically incorrect, it was also extremely tight (made from a Lycra Spandex material), thus not breathable and uncomfortable. The construction method required also led to these shirts needing to be full-length, which can get hot and sweaty.

Not only does Lycra Spandex material require an extremely tight wear from the user, it's also unsightly and unfashionable and does not translate well to commercial use, since customers are not inclined to wear the garment as their only layer. By wearing an additional layer on top of the Lycra Spandex to cover the unsightly artificial material layer of the posture correction garment, the breathability issue is compounded with an additional layer of tightness. Due to this combination, individuals typically stop wearing Lycra Spandex made posture shirts, thus sabotaging the process of building good habits in postural alignment. All of these issues compound to discourage patient wear and compliance since each factor adds an additional negative feature.

One therapeutic method for correcting posture involves the body's proprioceptive sense. An organism uses proprioception to maintain an internal model of its body's orientation in space, a sort of mental avatar representing the mind's best guess as to how its physical limbs are moving. When the primary motor cortex signals the muscles to fire, it also emits an efference signal, also known as a corollary discharge. This second signal has been hypothesized to suppress the subsequent firing of sensory cortex networks when they are inevitably stimulated by the aforementioned motor movement. Therapeutically applied proprioception can be explained by intensifying and subsequently normalizing the afferent proprioceptive mobility-controlling input.

Rather than utilizing vertical straps, one form of the proprioceptive correction technique is the utilization of horizontal straps that contract the rhomboids and the upper trapezius in a horizontal motion that moves the scapula towards the spine and is thus anatomically correct. This natural postural correction is effective because it physically (through the anatomically correct means) corrects a wearer's posture and then passively influences the posture after it is corrected. This is achieved due to the natural tension that the horizontal straps exerts on the wearer, which makes it so that the wearer wants to be in postural correct form without the force of a vertical strap constantly pulling over the shoulder and down to the buttocks region.

Additional systems include U.S. Pat. Nos. 4,202,327, 4,957,103, 5,158,531, 5,451,200, 5,599,286, 5,718,670, 6,102,879, 6,213,922, 6,440,094, 6,676,617, 6,936,021, 7,134,969, 7,153,246, 7,395,557, 7,662,121, 7,871,388, 8,047,893, 8,083,693, 8,308,670, 8,516,614, 8,556,840, 8,795,213, 8,795,215, 8,887,315, 8,905,956, 8,910,317, 8,932,236, 9,009,863, 9,167,854, 9,168,167, 9,226,534, 9,439,459, 9,445,932, 9,456,919, 9,504,280, 9,883,703, 9,931,236, US20040107479, US20050197607, US20060000478A1, US20080134409A1, US20090062704, US20100192274A1, US20120078149, US20120174282, US20130047313, US20130053744, US20130090521, US20130103079, US20140058307, US20140100501, US20140221893 and US20150040286A1.

However, none of the prior art references provide a proprioceptive design that efficiently correctly a wearer's postures. There exists a need for a more comfortable and proprioceptive woven fabric posture re-balance garment that corrects a wearer's posture using anatomically correct movement that allows for shoulder mobility, is breathable and aesthetically pleasing to promote patient compliance, and is not so tight as to be hot and uncomfortable to wear.

Accordingly, the present invention is a device directed to solving all of these problems.

SUMMARY OF THE INVENTION

It is an object of the present invention to provide a more comfortable, stylish, and proprioceptive woven fabric wearable technology using proprioceptive posture re-balance design, device, function, and method of manufacturing thereof.

It is an object of the present invention to provide a more comfortable and proprioceptive woven fabric posture re-balance garment that can be used alone or integrated into any other garment.

It is an object of the present invention to provide a more comfortable and proprioceptive wearable technology design and function using woven fabric posture re-balance garment and method of manufacture thereof that corrects a wearer's posture using anatomically correct movement that allows for shoulder squaring, eliminates slouching, increase shoulder and neck mobility, is breathable and aesthetically pleasing to promote wearers' compliance, is not so tight as to be hot and uncomfortable to wear and can be integrated into any garment.

It is an object of the present invention to provide a wearable technology garment and method of manufacture thereof that addresses the concern of a lack of patient compliance because it uses horizontal tension rather than vertical tension for correct anatomical posture correction and it can be integrated into any garment, thus allowing for breathability, a greater selection of garments for aesthetic appeal, and achieves a better upright stance and function of the human biomechanics and kinesiology in activities of daily living (ADL), and better quality of life for patients suffering from neck, shoulder and spine injuries.

Objects of the invention are achieved by providing a wearable technology garment device for correcting a wearer's posture, the garment device comprising: a mesh body; and a variable tension poly-elastic strap having at least one seam affixed to the strap, wherein the variable tension poly-elastic strap is configured to correct the wearer's posture by naturally pulling the scapula into correct postural alignment.

In certain embodiments, the mesh body is breathable.

In certain embodiments, the mesh body is of variable size(s).

In certain embodiments, the variable tension poly-elastic strap is of various size(s).

In certain embodiments, the mesh body is of variable size(s) and the variable tension poly-elastic strap is of various size(s). In certain embodiments, the variable tension poly-elastic strap is of various thicknesses based upon the size and posture of the wearer.

In certain embodiments, the mesh body is sized and shaped to cover at least the upper torso of a wearer's body. In certain embodiments, the mesh body is sized and shaped to cover the entire torso of a wearer's body. In certain embodiments, the mesh body is sized and shaped to cover the back, the chest, the sides of the torso, the arms, the shoulders, and/or portions thereof.

In certain embodiments, the garment technology design and function device is constructed to cover the chest, the neck, the back, the shoulders, the arms, the hips, and the lower body, and/or portions thereof. In certain embodiments, the garment device is constructed as an opened garment that covers the back, the neck, the shoulders, the arms, and the lower body and/or portions thereof. In certain embodiments, the garment device is constructed as an opened garment being opened at the chest portion or lacking the central portion of the chest.

In certain embodiments, the mesh body wearable tech may be designed and constructed as stand along garment or as an inner lining for various apparel clothing forms selected from all garments including all gender wear, upper and lower body wear, upper body and lower body apparel coverage, ranging from apparel used for undershirt, under wear, and outer wear apparel.

In certain embodiments, the mesh body includes a vertically segmented variable tension poly-elastic strap in various sizes and shape, length and width. In certain embodiments, the mesh body includes a plurality of variable tension poly-elastic straps.

In certain embodiments, the strap is manufactured from a material that is 78% polyester and 22% nylon-elastic. In certain embodiments, the strap may be manufactured from a material that is 70% polyester and 30% nylon elastic. In certain embodiments, the strap may be manufactured from a material that is 90% polyester and 10% nylon elastic. The strap material can be made from a combination of variable fabric including variations of polyester, nylon-elastic, other synthetic or non-synthetic, or organic materials.

In certain embodiments, the variable tension poly-elastic strap is provided mounted in the posterior portion of the garment device. In certain embodiments, the variable tension poly-elastic strap is provided mounted in the upper posterior portion of the garment device. In certain embodiments, the strap can extend above or below from superior angle of the scapula to above or below the scapular spine or above or below the inferior angle of the scapula. In one or more embodiments, the strap is provided within the device such that in use, the strap extends primarily along the scapular rotators, the rhomboids, the upper trapezius, the middle trapezius, the serratus anterior, the latissimus dorsi, and/or the deltoid muscles of the wearer. In certain embodiments, in use, the strap disposed about a wearer's upper back, shoulders and/or posterior of the arms. In certain embodiments, in use, the strap is constructed to end few vertebrae above or below the T-6 vertebrae of a wearer's spine.

In certain embodiments, the width of the poly-elastic strap is between about ½ inch inches to about 6 inches, pending on body anatomy.

In certain embodiments, the garment device includes at least two seams, and wherein the at least two seams are evenly spaced along the variable tension poly-elastic strap.

In certain embodiments, the garment device includes at least four seams and wherein the at least four seams are evenly spaced along the variable tension poly-elastic strap.

In certain embodiments, the garment device includes more or less than two seams or multiple seams. In certain embodiments, the garment device is seamless.

In certain embodiments, the garment device includes one or more than one integration intersection(s) to attach to a secondary garment, such as a shirt or outer garment.

In certain embodiments, the garment device includes a plurality of integration intersections to attach to a secondary garment, such as a shirt or any outer garment.

In certain embodiments, the mesh body in the garment device is made from materials chosen from the group consisting of nylon, spandex, cotton, polyester, chiffon, denim, lace, leather, wool, or a combination of synthetic, non-synthetic, organic, non-organic, thereof.

In certain embodiments, the wearer's posture is substantially improved physically and proprioceptively with the garment device.

In certain embodiments, the wearer's posture is corrected physically and proprioceptively with the garment device.

In certain embodiments, the garment device is configured to be conveniently integrated with a secondary garment device or an outer garment via at least one integrated intersection, wherein the at least one integrated intersection is located at a position chosen from a group consisting of: along the neck collar, nuchal point, upper along the axilla, around the midsection, bottom of the outer garment or a combination thereof. It can be integrated along the seam of the outer shirt or can be stand along lining with just one or combination of integration points In certain embodiments, the integrated intersections are along the collar of a shirt, underneath the armpit of a wearer, along the side of the midsection of the shirt, along the inner seams of a shirt and combinations thereof.

In certain embodiments, the variable tension poly-elastic strap is oriented in a manner chosen from the group consisting of: primarily horizontal, primarily vertical, primarily diagonal, or a combination thereof.

In certain embodiments, the mesh body has a variable length not limited to the following: a shortened length stopping just above or below the chest, an extended length stopping above or below the waist, and a medium length above or below the bellybutton/midsection length, and can be of matching length or less length of the outer garment.

In certain embodiments, the variable tension poly-elastic strap provides postural support to a wearer suffering from less than ideal posture, or suffering a related malady selected from the following group consisting of: rounded shoulders, slouching, scapular dyskinesis, flexible kyphosis, forward head, lordosis, scoliosis, rounded shoulder from cervical spine injury, rotator cuff tears, shoulder pathologies, acromioclavicular joint separation, arthritis, occipital neuralgia, cervical pathologies, overhead sports injuries, and general posterior musculature weakness.

In certain embodiments, the variable tension poly-elastic strap provides postural support to a wearer suffering from rounded shoulders from cervical spine pathology, rotator cuff, shoulder pathology, including but not limited to, AC Joint, Arthritis, AC Separation, upper back muscle spasm, and lower spine spasm.

In certain embodiments, the garment device corrects the wearer's posture through a form of direct physical therapy and indirectly through proprioceptive feedback.

In certain embodiments, the garment device includes a casing integrated into the poly-elastic strap. In certain embodiments, the casing envelopes the poly-elastic strap to provide comfort to a wearer. In certain embodiments, the casing is made of the fabric of a secondary garment to which the garment device is connected to or sewn into.

In certain embodiments, the garment device corrects the wearer's posture by pulling (retracting) the shoulder of the wearer to the posterior, thus placing the scapula in the proper anatomical location. In certain embodiments, the garment device corrects the wearer's posture by narrowing the distance between the left and right scapula. In certain embodiments, the distance narrowing between the left and right scapula is of at least about 3 mm, and in certain embodiments, the scapular muscle is more relax, and in certain embodiments, the erector spine muscle is more active to better support the upright posture stance.

In certain embodiments, the mesh body includes sleeves, wherein the sleeves of the mesh body extend at least below the deltoid of the wearer. In certain embodiments, the mesh body includes sleeves, wherein the sleeves of the mesh body extend to fit a long sleeve or short sleeve shirt. In certain embodiments, the mesh strap lining garment device can be sleeve free or with variable length of sleeve.

In certain embodiments, the garment device is configured to be sewn or attached into any existing item of clothing, is pre-sewn in a production pipeline, or comes standalone.

In certain embodiments, the garment device includes anti-microbial materials, moisture wicking materials, chemical elements, or a combination thereof.

In certain embodiments, the variable tension poly-elastic strap is designed to relieve all tension in the garment device when the wearer is standing, sitting, or in any ADL with correct postural alignment. In certain embodiments, the variable tension poly-elastic strap can have variable posterior pull or retraction. In certain embodiments, the garment device allows for a full range of motion for the wearer and the restriction of movement is minimized.

In certain embodiments, the garment device is configured to be sewn into a secondary garment and is graded specifically for different ranges in garment device size via corresponding different lengths of the poly-elastic strap and/or of the mesh body. In certain embodiments, the garment device is configured to be attached to a secondary garment via the at least one integrated intersection.

In certain embodiments, the garment device assists the wearer for shoulder muscle rebalance, shoulder rehabilitation, shoulder recovery, shoulder training, scapula rebalance, and/or muscular tension rebalance.

In certain embodiments, the garment device corrects muscolo-skeletal realignment, which in turn improves range of motion, and increase blood circulation in the wearer.

In certain embodiments, the variable tension poly-elastic strap and the breathable mesh of the garment device are configured to improve athletic performance. In certain embodiments, athletic performance is improved because as a wearer's movements become more efficient due to improved posture, and muscle relaxation and activation re-balance.

In certain embodiments, the garment device is form-fitting and designed to conform to the wearer's body.

In certain embodiments, the garment device supports the performance, posture and recovery in the wearer.

Other objects of the invention are achieved by providing a method of innovative inner lining garment design and manufacturing such garment device for correcting a wearer's posture, comprising: providing a mesh body; inserting a variable tension poly-elastic strap with at least one vertical seam into an elastic strap with or without casing that is stitched onto the mesh body, wherein the variable tension poly-elastic strap is configured to correct the wearer's posture by naturally see saw tension with pulling portions of the musculo-skeletal frame into correct postural alignment.

In certain embodiments, the variable tension poly-elastic strap includes one or more vertical seams. In certain embodiments, for devices for women, the variable tension poly-elastic strap includes multiple seams. In certain embodiments, for devices for men, the variable tension poly-elastic strap includes multiple seams. In certain embodiments, more or less seams are provided. In certain embodiments, the seams are evenly spaced. In certain embodiments there are no seams.

In certain embodiments, the mesh body is replaced by a similar material providing sufficient tension or rigidity.

In certain embodiments, the variable tension poly-elastic strap is integrated into the mesh body to allow for a wearer's forward range of motion. In certain embodiments, the mesh body can be used as a stand along garment without a tension strap, pending on the wearer's anatomy.

In certain embodiments, the length of the variable tension poly-elastic strap is graded specifically to each garment size. In certain embodiments, the elastic strap is configured around the medial point of the scapula of the wearer.

In certain embodiments, a casing is integrated into the construction of the elastic strap to provide comfort to the wearer.

In certain embodiments, the type of stitching method is chosen from a group consisting of: blind, double blind, flatlock, overlock, welded, active, or a combination thereof.

Other objects of the invention are achieved by providing a method for simultaneously passively and actively influencing a wearer's posture through biasing muscle forces, comprising: providing a mesh body providing sufficient tension or rigidity, the mesh body made from materials chosen from a group consisting of: nylon, spandex, polyester, or a combination of the above and other materials; providing an elastic strap integrated into the mesh body, wherein the elastic strap creates a variable tension force between at least one focal points in a wearer.

Other objects of the invention are achieved by providing a posture recovery daily wear apparel consisting of a garment device stand alone or as a lining of an outer garment made concomitantly for daily wear and for training and retraining of muscle balance to improve a user's posture. The inner lining and outer apparel combined design, function and method of manufacturing provide an innovative game changing wearable technology for posture training or re-balance in daily wear, unconsciously. The garment device comprising: a mesh garment made from mainly nylon and spandex; and a variable tension poly elastic strap with variable spaced, vertical seams to target and disperse tension in a wearer.

In certain embodiments, the mesh garment has a shortened length, stopping just above or below the chest. In Certain embodiments, the inner mesh strap device is made to match length of the outer apparel.

In certain embodiments, the variable tension poly elastic strap provides support to the wearer. In certain embodiments, the variable tension poly elastic strap provides support to the wearer's posture by naturally pulling the scapula into correct postural alignment.

In certain embodiments, the variable tension poly elastic strap is incrementally adjusted to improve the wearer's posture in set intervals.

In certain embodiments, the correction of a wearer's posture is corrected proprioceptively. In certain embodiments, the device corrects the wearer's posture by pulling the shoulder of the wearer closer the spine, more posterior, thus placing the scapula in the proper anatomical location.

In certain embodiments, the device improves athletic performance. In certain embodiments, the device contains combination of chemical materials, anti-microbial materials, anti-moisture wicking materials and protects against ultraviolet (UV) rays.

In certain embodiments, the tension straps are designed to relieve all tension in the garment when the wearer is standing with correct postural alignment and cease the anterior slouching posture. In certain embodiments, the device allows a full range of motion for the wearer. In certain embodiments, the device can be sewn into any garment and is graded specifically for each garment size via a poly-elastic strap.

In certain embodiments, the device allows for ease of breathing and a more comfortable fit. In certain embodiments, the device assists the wearer in muscular tension rebalance.

In certain embodiments, the device assists the wearer for shoulder muscle rebalance, shoulder rehabilitation, shoulder recovery, and/or shoulder training. In certain embodiments, the device assists the wearer with scapula rebalance. In certain embodiments, the sleeves of the device do not extend below the biceps of the wearer.

In certain embodiments, the device improves the efficiency of a wearer's posture which increases blood circulation in the wearer and promotes health and general physical and mental well-being.

Other objects of the invention are achieved by providing a method for creating a wearable technology garment device for correcting a user's posture, comprising: providing an inner lining mesh garment made from a combination of materials such as nylon and spandex; inserting a variable tension poly elastic strap with or without vertical seams into the mesh garment, with or without casing, wherein the variable tension poly elastic strap targets and disperses tension in a wearer. The garment device can be used stand along or combined into an outer apparel for daily wear.

In certain embodiments, the elastic strap is graded specifically to each garment size. In certain embodiments, the elastic strap is configured around the superior and inferior borders or near medial points of the scapulae.

In certain embodiments, the mesh body garment has an under-layer or an inwardly facing surface designed to resist slippage when donned. The mesh body is required to encase the wearer's upper body and therefore can benefit from an inner surface that adds small, diffusing force by wrapping around the chest and shoulders, which distributes force evenly across the shoulder capsule.

In a certain embodiment, the mesh body includes a combination of nylon and spandex, or combination of various materials. In a certain embodiment, the mesh body includes between about 25% and 90% of nylon and between about 10% to about 40% of spandex, and combination of various percentage of materials.

Other objects of the invention are achieved by providing a garment device constructed with a strong power mesh made from 72% nylon and 28% spandex in its current embodiment and designed with a short and loose construction that stops just below the pectoralis major and T-8 vertebrae. The garment device does not restrict movement of the shoulder, neck, or spine, as the other tight-fitting posture garments in this space do.

Other objects of the invention are achieved by providing a garment device constructed with a strong power mesh made from approximately 70% nylon and approximately 30% spandex in its current embodiment and designed with a short and loose construction that stops just below the pectoralis major and T-8 vertebrae. Despite the mesh, the garment device does not restrict movement of the shoulder, as the other tight-fitting posture garments in this space do.

Other objects of the invention and its particular features and advantages will become more apparent from consideration of the following drawings and accompanying detailed description. It should be understood that the detailed description and specific examples, while indicating the preferred embodiment of the invention, are intended for purposes of illustration only and are not intended to limit the scope of the invention.

BRIEF DESCRIPTION OF THE DRAWINGS

FIG. 6A-6B are posterior anatomical views of the back and shoulder musculoskeletal architectures.

FIG. 7A-7B shows the garment device pulling the shoulders or a wearer.

DETAILED DESCRIPTION OF THE INVENTION

Figures 1A, 1B:
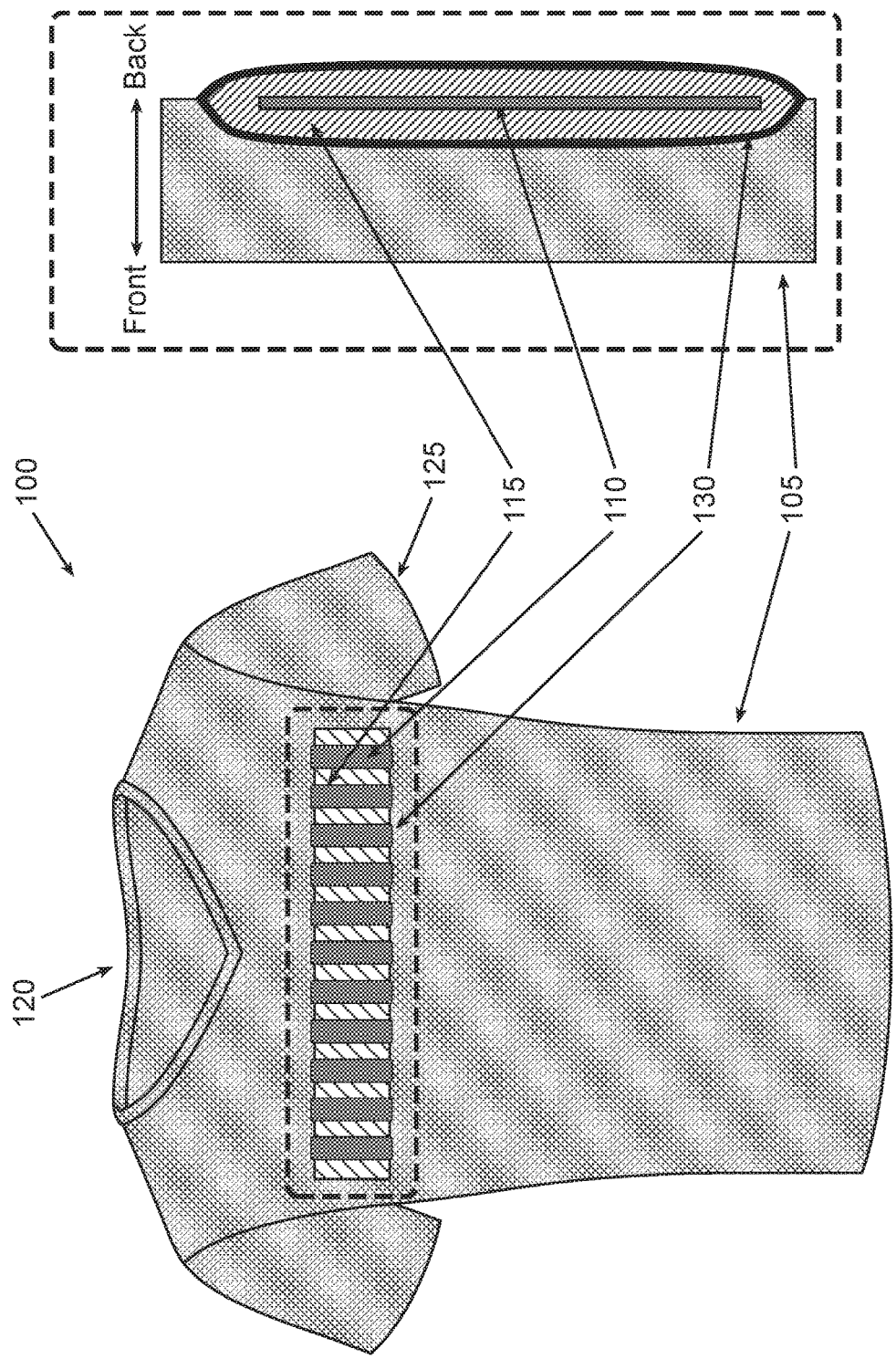
FIG. 1A-1B is an anterior view of the garment device and a zoomed in side-ways view of the elastic strap inside the casing.

The present invention is directed to a wearable garment device that accounts for the limitations of the currently available garments made with Lycra Spandex and other constricting materials. Branded as PPR—posture, performance, recovery, and IFG-I Feel Good, —this is a device that accounts for all four namesake items in its title: (1) proprioceptively correcting a wearer's posture; (2) giving wearers better performance with more motion generated power via better posture and anatomy form; (3) allowing for better recovery via correction of poor posture habits, and (4) the wearer feels good with energized muscle rebalance and lessen muscle tension in the neck and shoulder. The garment improves upon previous posture garments through its flexible nature, namely the ability to act as a garment addendum device, i.e. it can be conveniently sewn into any existing garment at the time of the manufacturing using wearable technology or come pre-packaged and integrated into another manufactured garment fresh off the production line. Not only does this single handedly solve the problem of unaesthetically pleasing posture garments plaguing the space since its inception (as the garment device is nearly unnoticeable and can accommodate any common garment), it does so while also solving the issues of shoulder rounding, slouching, restriction and non-breathability through allowing a full range of motion.

The garment device is unisex and not limited by a sizing factor, therefore it is also flexible in the way it corrects a wearer's posture. In other words, the garment device is custom fitted for each wearer by being sewn into the inside of the chosen garment, at various integrated intersections such as near the neck opening area or armpits. For correcting rounded shoulders, an elastic strap is sewn horizontally across the areas of the garment that correspond to connecting the medial points of each scapula, also known as the "shoulder blade". Thus, patients or casual wearers are no longer tasked with finding the specific matching size and overly complex posture correcting garments; they can simply sew any garment device into their own chosen garment.

Aside from its flexible nature of fabrication in accommodating any garment for usage, the garment device achieves its main function of posture correction through a proprioceptive manner that involves creating a substantially parallel amount of tension in the body's anatomical musculature. The garment device mirrors and augments the muscle groups of the scapular rotators, spine muscles, Latissimus dorsii, Rhomboids, Trapezius, Posterior Deltoids, Teres Minor, Subscapularis, and Teres Major, among others to create a pull that naturally assists the wearer into scapula adduction (also known as retraction) for correct postural alignment. Once the wearer is in correct postural alignment, the garment device automatically relieves all tension in the garment and ceases the pull that gives the wearer correct posture in the first place. Thus, the wearer will barely notice the device once the wearer has achieved the muscle memory of correct posture. The main objective is bringing the shoulder blades closer together, closer to the spinous process, and thus bringing the head into a more posterior position, anatomically aligned over the spine, and lessen tension on the neck and shoulder muscles The variable elastic strip of the garment device mimics the anatomical motion of the scapular rotators and spinal muscle groups. This is what applies the intense afferent signal to the proprioceptive system, thereby training the system. It is accomplished by the elastic strap cycling between a relief of tension and exertion of tension on the parallel muscle system.

Additional advantages of the garment device include:

"Improves Performance"—It is contemplated that the garment, by retracting the scapula, will assist in weight lifting training regimens and competition, by improving the wearer's form throughout the lift. A retracted scapula creates a more stable base and results in the recruitment of relatively more chest muscle groups, as opposed to the weaker shoulder muscle groups. Due to the user recruiting a stronger muscle as the primary mover for an exercise, there will be faster progress in training and improved performance for competitions.

"Seesaw effect"—As one treatment option, posture shirts were created to fill the burgeoning need of proprioceptive therapy. Posture shirts typically contain elastic straps and special stitching that helps maintain an upright body with correct alignment both skeletal and muscle-wise through the contraction and relaxation of certain muscles. Natural posture alignment in the thoracic spine is achieved when posterior muscle groups (i.e. trapezius, rhomboids, latissimus dorsi) and anterior muscle groups (serratus anterior, etc.) are both exerting the same amount of force, thus allowing the body to be balanced.

Aside from its flexible nature in accommodating any garment for usage, the garment device achieves its main function of posture correction through a proprioceptive manner that involves creating a parallel amount of tension in the body's anatomical musculature. The garment device mirrors and rebalance both scapular and spinal muscle groups to create an activation and relaxation of appropriate muscle groups that naturally assists and maintains the wearer into scapula adduction (also known as retraction) for correct postural alignment. Once the patient is in correct postural alignment, the garment device automatically relieves all tension in the garment and ceases the multi-pull that gives the wearer correct posture in the first place. Thus, the wearer will barely notice the device once the wearer has achieved the muscle memory of correct posture.

"Attachment point" or integrated intersection—The main attachment point (integrated intersection) is chosen along the posterior rim of the collar, because this point of contact between the two garments is the most stable and least likely to experience shifting. The anatomical position of the attachment point is the nape of the neck, otherwise referred to as the "nuchal" point in medical terminology. In other embodiments, the potential attachment points include the areas circumscribing the upper seam of the shoulder, the neck, possible axilla and possible anterior pectoris. In other embodiments, pending anatomy of the wear, the inner garment integration point can be selective to be one to various points along the seam of the outer garment.

Posture and Proprioceptive Therapy—the garment devise provides improved results for musculature around the shoulder and spine. The shoulder, or glenohumeral joint, provides the arm with a large range of motion, yet this joint possesses very little intrinsic stability, resembling a ball on a plate more than a ball in a socket. Most stability in the shoulder is provided by the ligaments and muscles surrounding the joint. Proper muscle activation and relaxation are necessary to maintain positioning scapula and shoulder joint. Adjustments are continuously made to glenohumeral joint position based on feedback information from proprioceptive receptors in the muscles, tendons, ligaments, and receptors in the skin. Proprioception is a complex entity with many interacting components. The brain uses efference copy to initiate and verify active motions. Such verification requires information about musculoskeletal motion sent back to the brain by a variety of sensory receptors in the muscles and skin. The current belief is that muscle spindles, movement encoders in parallel with the muscle, are the predominant proprioceptors with important contributions from cutaneous receptors. Muscle spindle intrafusal fibers in the shortening muscle contract during active motion, possibly to maintain muscle spindle sensitivity.

Scapular rotators and spinal muscle retraining therapy—
The scapular rotators and spinal muscles provide stability of posture in ADL and in sports performance. Rhomboid and Trapezius muscles of the shoulder blades are also responsible for the retraction of the shoulder blades. Those muscle groups contract and draw the scapula towards the spine thus drawing the whole shoulder toward the posterior. Most people with less than desirable posture do not adequately contract or rebalance the aforementioned muscle groups to maintain neutral anatomy and proper posture. The garment device consists of two primary types of fabrics that mimic the motion and contraction of the scapular rotators and spinal groups. The vertically segmented elastic strap is mounted in the center, posterior of the garment device. The vertically segmented elastic strap precisely overlays the rhomboids, upper and middle trapezius. When the shirt is donned by the user, the elastic strap is slightly stretched (or extended). Due to the stretch of the elastic, pull is created toward the spine, mirroring the contraction and relaxation of the scapular rotators and spinal muscle groups in combination to provide better posture and shoulder blade alignment. If the user holds perfect posture with his/her own musculature the vertically segmented elastic strap applies very little pressure. As the user allows his/her shoulders to "roll" forward, the vertically segmented elastic strap applies greater tension.

The garment device mesh body (or similar fabric) encapsulates the upper arm, shoulder and upper back. This allows the Vertically segmented elastic strap to attach to the medial point of the scapula. The tension and force of the strap is distributed across the entire front and rear shoulder area diffusing uncomfortable pressure points and providing retraction by "pulling" from the front and rear of the shoulder simultaneously.

This method of retraction differs from other products. Competitors use vertical straps sewn into a garment that run from the upper shoulder or chest, down the back and terminating at the buttox. The force of these straps are applied to the upper insertion points of the straps (which they call NeuroBands). The problem with these types of shirts is that the entire body has to be tight and if the wearer does not exactly fit the garment it is ineffective. The garment device's benefit is that it applies diffused horizontal tension that mirrors the anatomy and the body of the garment can be loose or tight depending upon the user's preference.

Thus, the present invention provides, in a first aspect, a garment device for correcting a wearer's posture, the garment device comprising:

a mesh body; and a variable tension poly-elastic strap configured to correct the wearer's posture by pulling the scapula into correct postural alignment.

The mesh body of the herein disclosed garment may be constructed as a shirt (such as a T-shirt) configured to cover the torso and specifically the back and/or chest and/or torso sides, or portions thereof. The mesh body is further configured to cover the arms, and/or shoulders, or portions thereof. Optionally, the garment may be constructed as an opened shirt, optionally essentially lacking the central chest portion. In such configuration, the garment may present the form of a tight top cloth that covers the back, shoulders, and/or arms, or portions thereof. The mesh body may thus present various forms of garment configuration. The mesh body can be stand-alone garment or sewn into an outer garment at the time of the production of the outer garment with technology displayed here.

In certain embodiments, the mesh body includes sleeves. Various sleeve lengths are contemplated. For example, the sleeves' length may extend at least below the deltoid of the wearer. The sleeves of the mesh body may extend to fit a long sleeve or a short sleeve shirt. In certain embodiments, the mesh body is sleeveless.

The mesh body may present variable lengths and various coverage of the outer garment. The length can be selected from a group consisting of: a shortened length stopping just above or below the chest, a shortened length stopping just above or below the inferior angle of the scapula, an extended length stopping below or about the waist, and a medium length stopping at or about the lower back/bellybutton. The mesh body integration into the outer garment may be present as inner lining of back of the outer garment and not present in the front of the outer garment, or it can be present as the inner lining of the entire outer garment, or in various combination.

The mesh body is configured such that it has a comfortable slim body fitting. The mesh may be very thin making it invisible under even the thinnest of secondary or outer garments. The thin nature of the garment device also allows it to be adapted to any style of shirt.

Advantageously, the body of the garment is constructed from a breathable fabric such as a mesh, allowing improved comfort and appearance. Provided with various optional degrees of textures and fabrics and depending upon the force and tension required based upon the chosen activity, the body habitus, anatomy, the mesh can be constructed to have various tension to allow more posture alignment or just being soft and supple.

Various types of fabric materials are contemplated and can be used as the mesh body in the herein disclosed garment. For example, the mesh body may be made from materials chosen from the group consisting of nylon, spandex, cotton, polyester, chiffon, denim, lace, leather, wool, or a combination thereof. In a certain embodiment, the mesh body is made from a combination of nylon and spandex. In a certain embodiment, the mesh body may include between about 50% and about 90% of nylon. For example, between about 60% and about 90%, or between about 60% and about 80% of nylon. In a certain embodiment, the mesh body may include between about 15% and about 40% of spandex. For example, between about 15% and about 35%, or between about 20% and about 30% of spandex. In an exemplary embodiment, the mesh is made from about 70% nylon and about 30% spandex. In yet a further exemplary embodiment, the mesh body is made from about 72% nylon and about 28% spandex, and in combination with other materials synthetic or non-synthetic.

The garment device is configured to be conveniently integrated with a secondary garment or outer apparel via at least one integrated intersection. The device, once attached to a secondary garment or outer apparel can be donned easily, allowing the simultaneous wearing of the herein disclosed device as well as the attached secondary garment.

The garment device includes a mesh variable tension poly-elastic strap wearable technology which is the main posture correcting feature of the inner garment device. The strap may be manufactured from a stretchy fabric, such as a two way or a four way stretch. in certain embodiments, the strap may be manufactured from a material that is 78% polyester and 22% nylon-elastic. In certain embodiments, the strap may be manufactured from a material that is 70% polyester and 30% nylon elastic. In certain embodiments, the strap may be manufactured from a material that is polyester nylon spandex or other materials in combination. Additional variations of polyester and nylon-elastic are contemplated.

To regulate and disperse the tension of the strap, the strap may be segmented by either multiple vertical seams or no seams. Further, one or more seams which may be vertical and/or horizontal may be used to affix the strap to the mesh body. In an embodiment of the invention, the number of seams depends on the wearer's gender, size and/or degree of required posture correction. For example, one strap may require two or four vertical seams. The vertical seams create a plurality of segments within the strap. For example, the strap may include three or more, four or more, five or more, or six or more segments.

In certain embodiments, the variable tension poly-elastic strap is oriented in a manner chosen from the group consisting of: primarily horizontal, primarily vertical, primarily diagonal, or a combination thereof.

The orientation, position, and/or size of the strap along the garment is of an essential importance in effecting the posture correction. In an embodiment of the invention, the strap is attached to the upper back, and optionally also to the shoulder and/or arms of the wearer's body. In an embodiment of the invention, the strap allows retraction of the shoulder blades and facilitates force distribution over the entire shoulder. Further, the strap may eliminate uncomfortable tension points that are often associated with current posture correcting garments. The garment device with the elastic strap may also mimic the contraction and relaxation of the scapular and spinal muscle groups. In an embodiment of the invention, the strap is provided mounted in the posterior portion of the garment device. In one or more embodiments, the strap may be disposed and extend from the posterior superior angle of the scapular or base of the neck downwardly towards a center posterior of the garment device. In one or more embodiments, the strap may be disposed just below the neck. In one or more embodiments, the strap may be disposed along an upper back of a wearer, covering the entire shoulder blades. Alternatively, or additionally, the strap may be disposed about a wearer's shoulder blades and spinous process. In one or more embodiments, the strap may be disposed about a wearer's shoulder blades, and arms. The strap may be terminated above or below T-4-8 vertebrae of a wearer's spine. Optionally, the strap is constructed to terminate just below about, or just above about, or about the T-7 vertebrae of a wearer's spine. For example, the strap is can be constructed to start above C7-T6 vertebrae of a wearer's spine. In an exemplary embodiment, the strap can be constructed to end just above the T4 and below T-10 vertebrae.

In certain embodiments, the variable tension poly-elastic strap is of various widths based upon the size of the wearer and/or degree of required posture correction. The width of the poly-elastic strap may be within the rage of about 1 to about 8 inches. In an exemplary embodiment, the average width of the poly-elastic strap is about 4 inches. but can be of various width pending on wearer's shoulder anatomy.

The herein disclosed garment device effects vertical and/or horizontal scapular retraction toward the spinous processes and/or allows narrowing the distance between the left and right scapula. The herein disclosed garment device successfully affords narrowing the distance between the left and right scapula. As measured empirically, utilizing the Scapula Lennie test, the garment device presents, in average, about 11 mm (range of between about 5 mm and about 25 mm) narrowing of the distance between the left and right scapula. Thus, in certain embodiments, the herein disclosed device effects at least about 5 mm narrowing of the distance between the left and right scapula.

Figure 10:
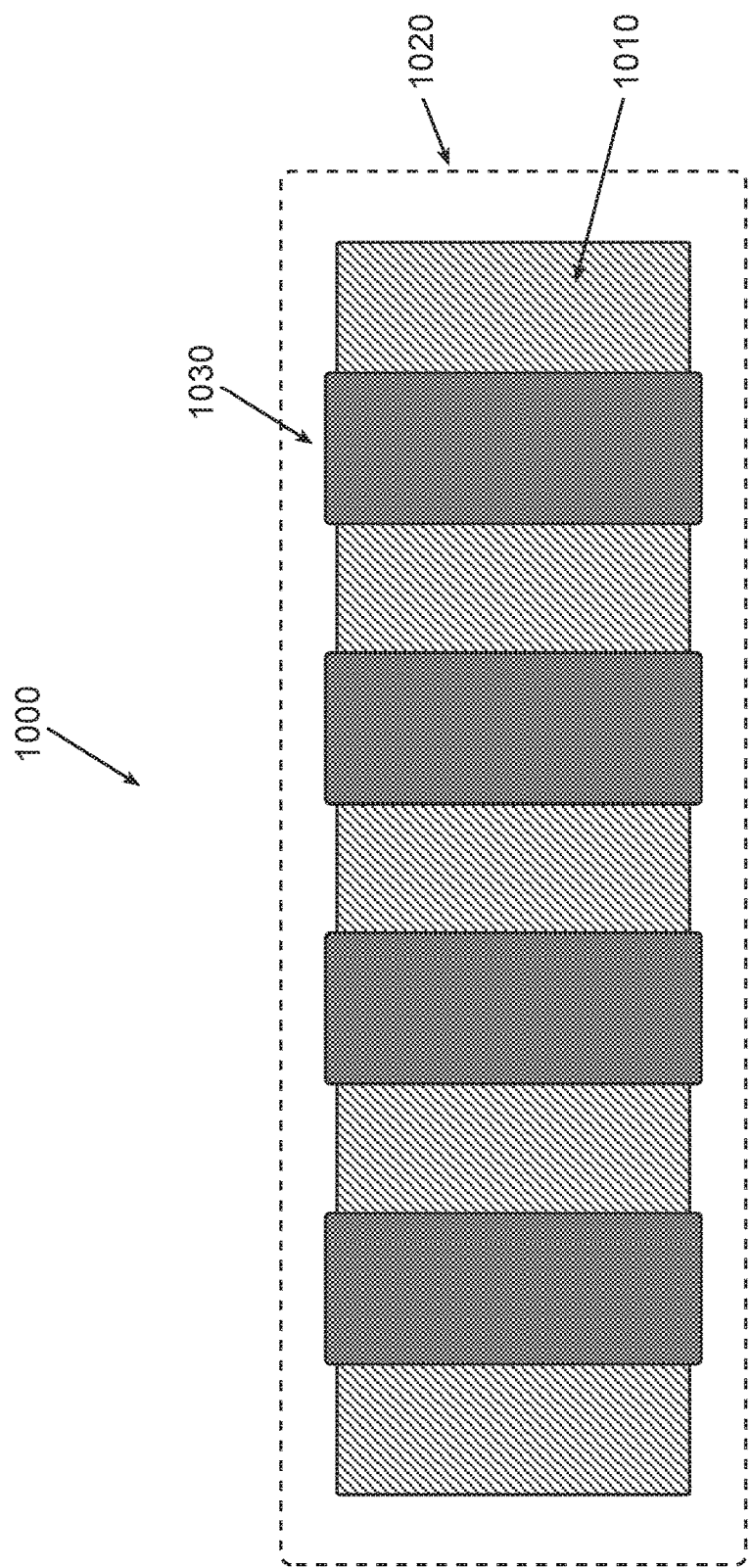
FIG. 10 shows the poly-elastic strap, casing and vertical seams according to an embodiment of the invention.

Referring now to FIG. 1, this is an anterior view of the garment device 100. It is made out of a strong power mesh 105, which can be composed of a variety of different fabrics and has moderately heavy compression qualities, creating an 'inner structure' lining device, that is sewn into a garment via one or more attachment points 120. The garment acts as an inner structure in that it is nearly unnoticeable inside both short and long sleeve garments. In its current embodiment, the garment device has arm seams 125 that stop just below the deltoid and at the mid-bicep level. The anterior and posterior shoulder of the garment is easy pull fitting and provides compression to the wearer. Although the current embodiment of the garment device is constructed in this fashion, the garment device can be adopted to fit a various length sleeves outer garment. Also shown in FIG. 1 is 110, which is a variable tension poly elastic strap. In certain embodiments, the strap has a thickness of 4 inches. Also shown are 115 which are the vertical seam lines. In certain embodiments, there are two vertical seam lines for garment devices for women and 4 seam lines for garment devices for men (see FIG. 10 showing the seams as vertical lines). Element 130 is the poly-tensile sheath casing which in certain embodiments envelopes the strap.

Figure 2:
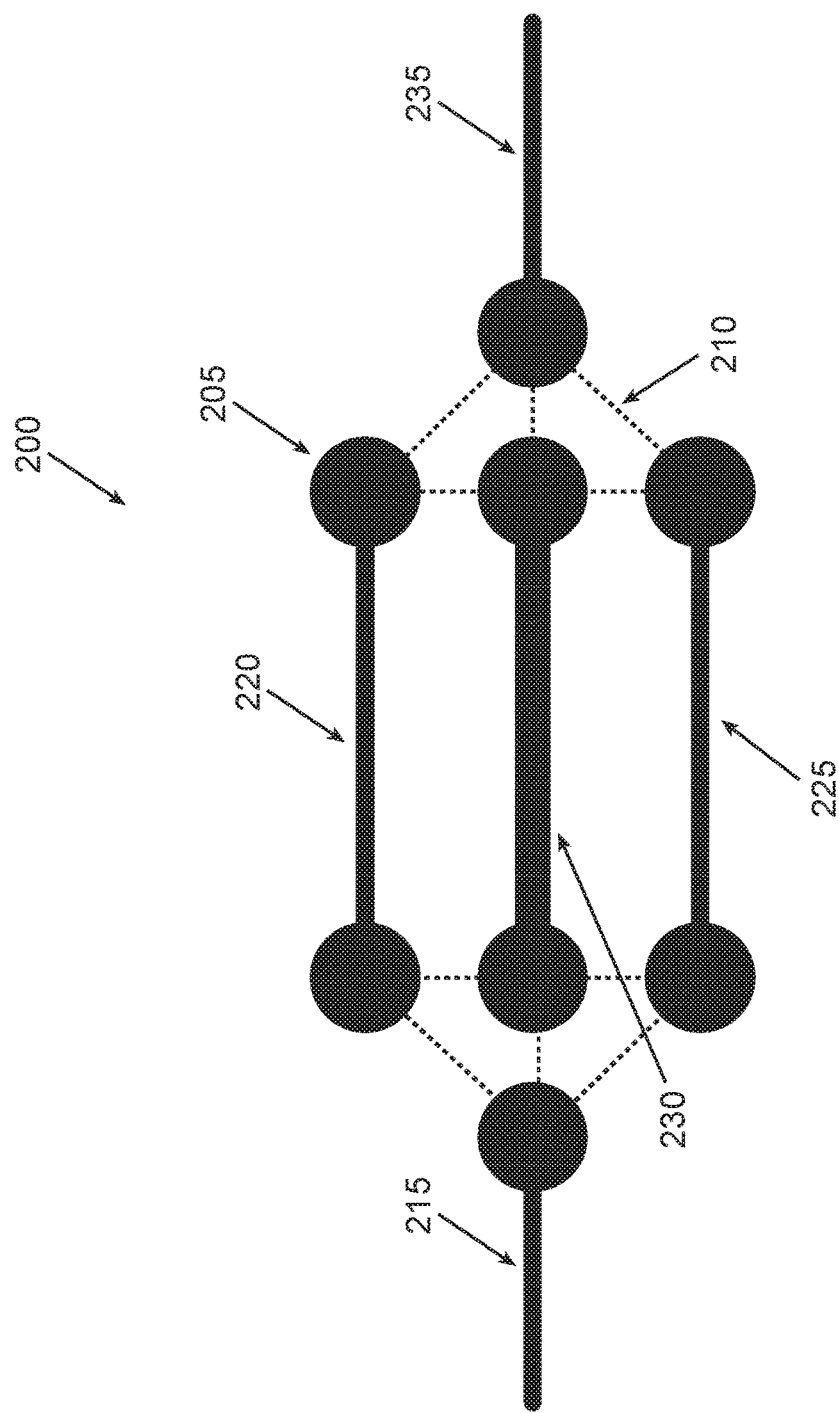
FIG. 2 is a schematic view of the elastic strap from the garment of FIG. 1.

Referring now to FIG. 2, the strap casing and device integration 200 is shown. A connection point (black circle) 205, stitching, either blind or welded (dotted lines) 210, superior mesh 215, exterior casing 220, interior casing 225, elastic strap 230, and inferior mesh 235 is shown. As demonstrated schematically, the elastic strap 230 is enveloped by the exterior casing 220, and interior casing 225 at opposing vertical edges thereof. Further demonstrated an embodiment wherein the horizontal opposing edges of the elastic strap 230 are stitched to superior mesh 215 and inferior mesh 235.

Figure 3:
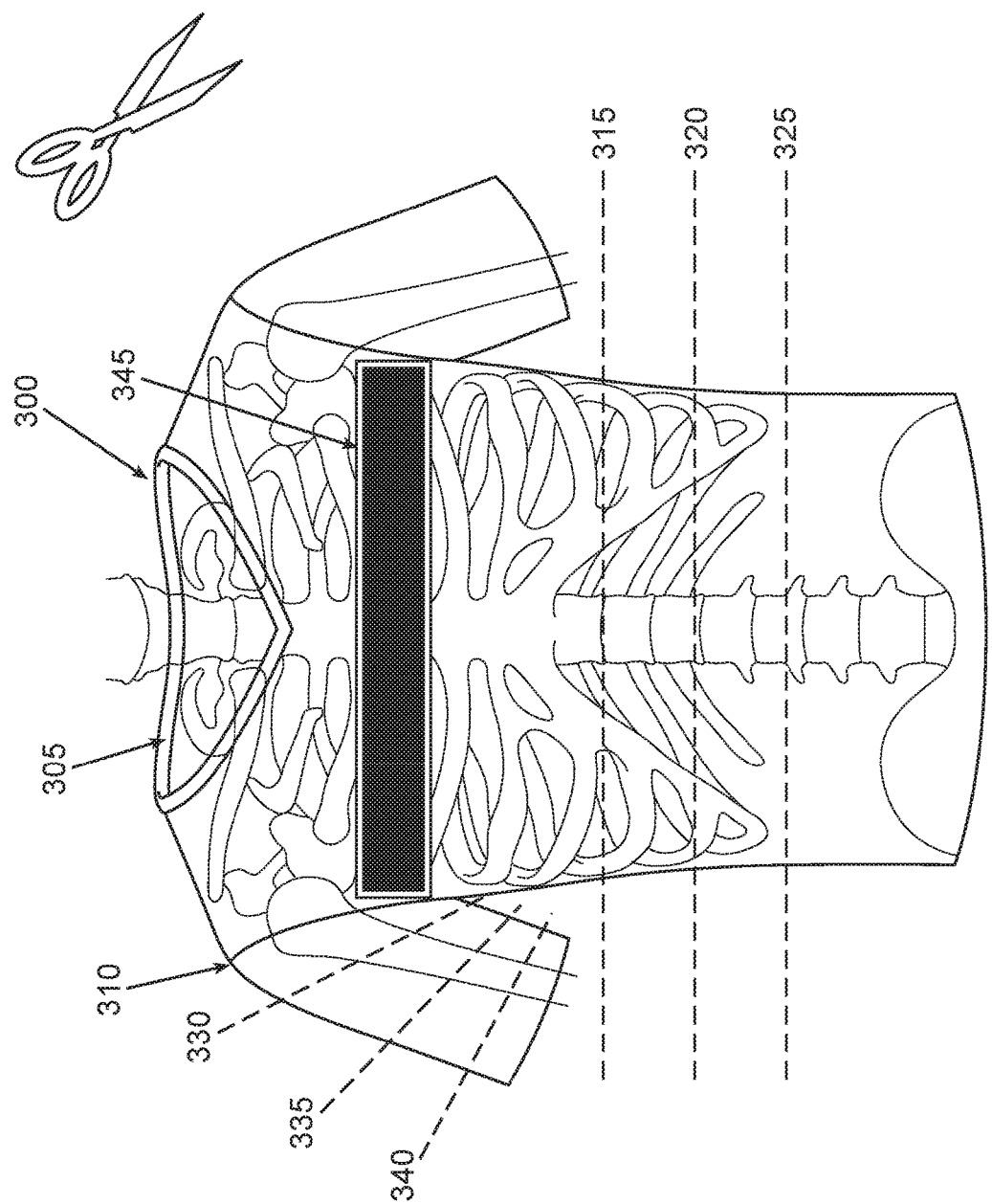
FIG. 3 is an anterior view of the garment device superimposed over a human skeletal model for biomedically tailored reference points.

Referring now to FIG. 3, this is an anterior view of the garment device. As it's connected to the back, the anterior portion of the device is made out of the same strong power mesh with the same sleeve length as the posterior of the garment. It has the same attachment point as the back of the garment, and just as the back, it's constructed with a shortened length—in this current embodiment stopping just below the T-8 vertebrae (can be below or above any T vertebras pending on the wearer's anatomy). There is a four-inch-wide poly elastic strap that is horizontally sewn into the garment, attached to the arm seam fabric such that each scapula is connected. This poly elastic strap is further segmented by four, evenly spaced vertical seam lines that regulate and disperse the tension of the strap, thus preventing the application of excessive force to the wearer when the shoulders are in neutral position. This poly elastic strap is sheathed by a casing that provides comfort to the wearer. In certain embodiments, the casing is made of the same fabric as a secondary garment to which the garment device is attached to.

Furthermore, the strap length is graded (sized) specifically to each garment size that the device is being sewn into, providing a custom-built solution to each piece of fabric and giving the wearer a comfortable way for proprioception with regulated shoulder retraction. The poly elastic strap assists the wearer in a natural, scapula retraction that uses the body to achieve correct postural alignment through mirroring and augmenting the muscles that are primarily associated with such contraction.

Referring now to FIG. 3, a full-length mesh body garment is shown superimposed onto a human skeletal model for biomedically tailored reference points 300. The primary attachment point, or integration intersection, is chosen along the posterior rim of the collar, because this point of contact between the two garments is the most stable and least likely to experience shifting. The anatomical position of the attachment point is the nape of the neck, otherwise referred to as the "nuchal" point in medical terminology. The device can be sewn in via nuchal attachment point 305 or axilla attachment point 310 to any traditional garment and essentially be unnoticeable to the casual observer. As shown in the embodiment of FIG. 1, the device has a shortened, chest length construction so that it can easily be sewn into any upper garment. More specifically, the garment device terminates just below the pectoralis major. However, in this embodiment it is shown with a longer length and three possible alternate termination points, 315, 320, 325. Similar to the shirt length, the sleeve length 330, 335, 340 can also be adjusted to the wearer's preference or the intended overlaying garment. While the elastic strap 345 is depicted in primarily the dimensions shown in the drawings as 4 inches wide, this width may vary in addition to the elastic material, in order to change the degree of tensile strength and resulting force applied to the wearer. The length of the elastic strap, however, should remain relatively constant, being altered only to accommodate variable sizes in the wearer. It is contemplated that variations will range from petite to large, although a custom elastic strap length can easily be fabricated.

It is contemplated that the garment, by retracting the scapula, will assist in weight lifting training regimens and competition, by improving the wearer's form throughout the lift. A retracted scapula creates a more stable base and results in the recruitment of relatively more chest muscle groups, as opposed to the weaker shoulder muscle groups. Due to the user recruiting a stronger muscle as the primary mover for an exercise, there will be faster progress in training and improved performance for competitions.

Figure 4:
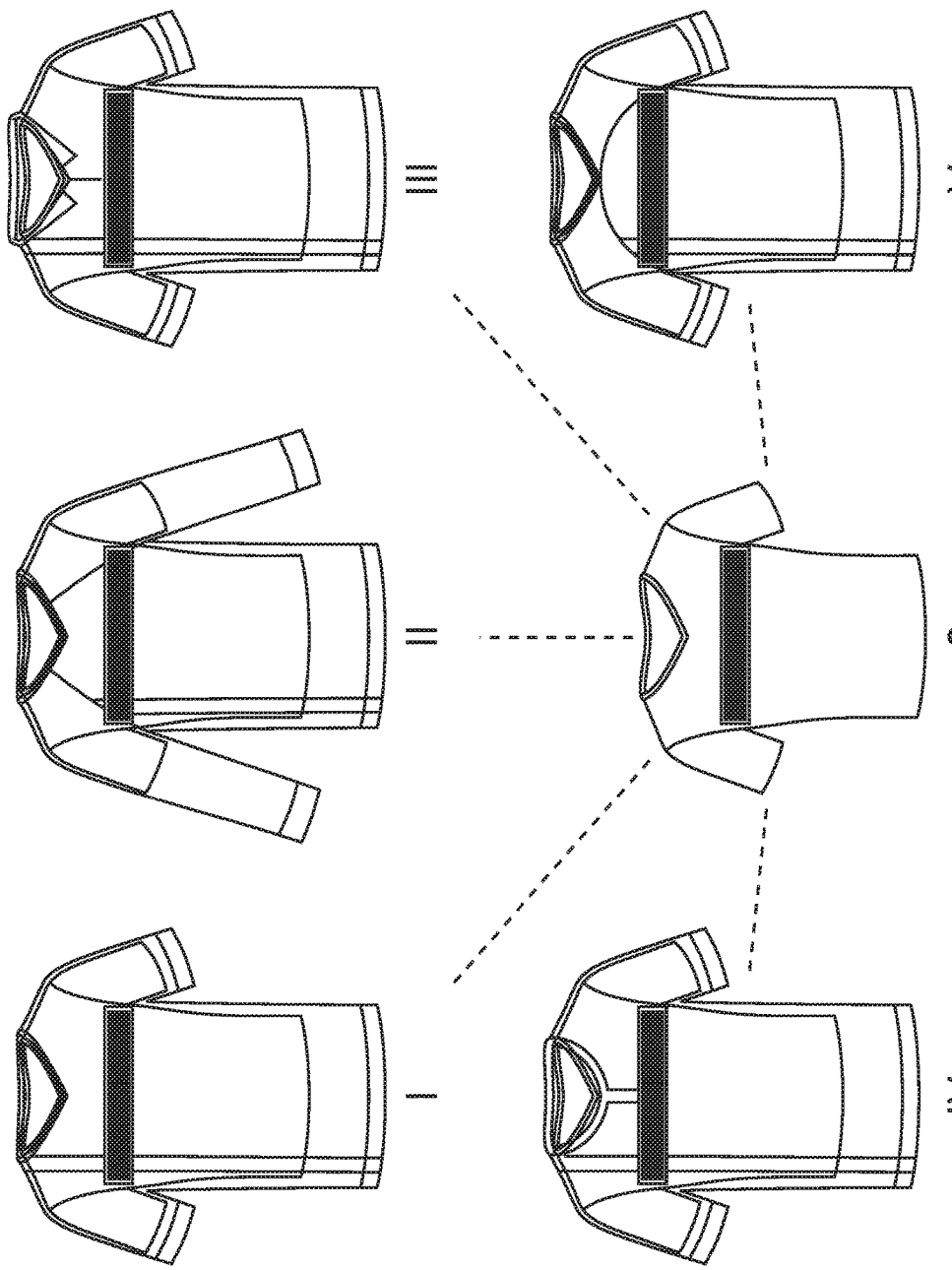
FIG. 4 is an anterior and translucent view of the garment device as sewn into multiple types of garments.

Referring to FIG. 4 are various types of garment (secondary garment) which the garment device is configured to be sewn into or manufactured into in a pre-assembled state.

Dynamic Proprioceptive Muscle Correction

Figure 5A:
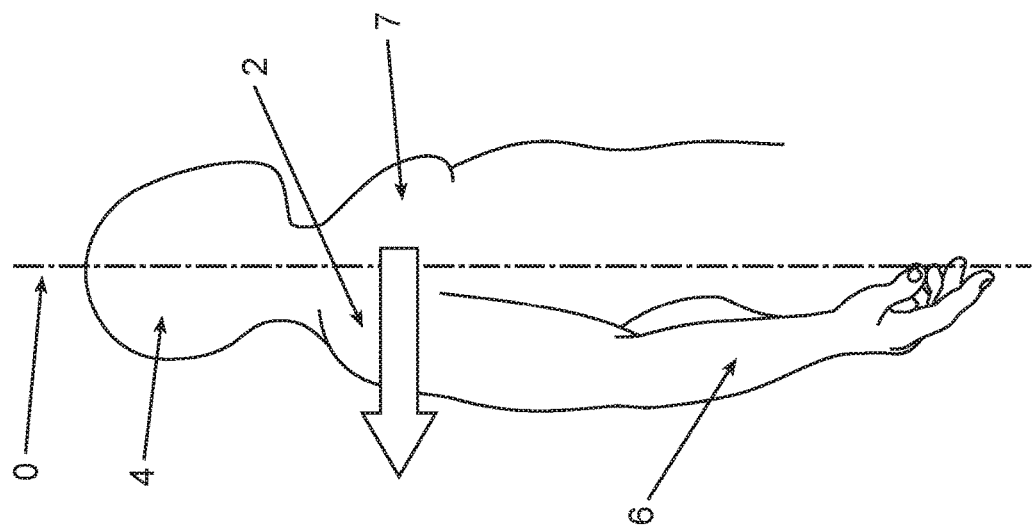
FIG. 5A-5B is a two-part diagram of rounded shoulders aka protracted shoulder girdle compared to good posture with relatively retracted scapulae.
Figure 5B:
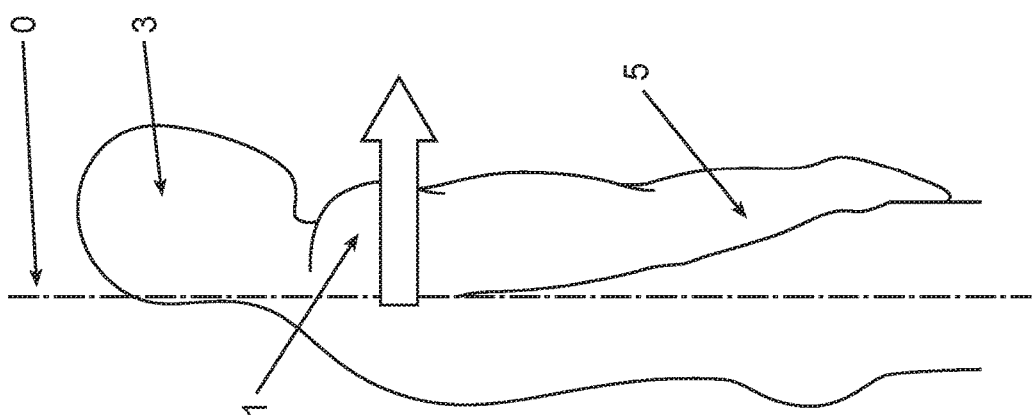

Referring to FIG. 5, a diagram of Rounded shoulders aka protracted shoulder girdle VS. Good Posture is shown. Elements shown are Midline 0, Protracted shoulders 1, Retracted shoulders 2, Compensatory head posture (stooping or tilting), chronic forward head posture, postural distortion, anterior head carriage 3, Correct head posture 4, Arms in front of midline 5, Arm behind the midline 6, Chest is more open and breathing enhanced 7.

FIG. 6A depicts the trapezius and rhomboid musculature and surrounding skeletal anatomy. FIG. 6B depicts the shoulder, also known as the glenohumeral joint, is the most flexible and mobile junction in the human body having up to 180 degrees of flexion; and as such is prone to several common malfunctions. The shallow glenoid cavity, while allowing maximum range of movement, is also extremely vulnerable to insults, thus the surrounding glenohumeral ligaments and muscles must be strengthened to a degree that will prevent dislocation.

FIG. 7A-7B depicts the mechanism of action and the dynamic effect 700 it has on a wearer's posture. The garment device consists of types of fabrics that mimic the motion, relaxation, and contraction of the scapular rotators and spine erectors.

The vertically segmented elastic strap 705, is mounted in the center, upper, posterior of the garment device. The vertically segmented elastic straps 705 and 710, precisely overlays the scapular rotators. When the shirt is donned by the user, the elastic strap 705 is slightly stretched (or extended). Due to the stretch of the elastic, pull 720 is created toward the spine, mirroring the rebalance of shoulder and spinal muscles. If the user holds perfect posture with his/her own musculature the vertically segmented elastic strap 710 applies very little pressure. As the user allows his/her shoulders to "roll" forward 715, the vertically segmented elastic strap applies greater tension 720.

The Mesh (or similar fabric) 725 encapsulates the upper arm, shoulder and upper back. This allows the vertically segmented elastic strap to attach to the medial point of the scapula. The tension and force of the strap is distributed across the entire front and rear shoulder area diffusing uncomfortable pressure points and providing retraction by "pulling" from the front and rear of the shoulder simultaneously.

This method of retraction differs from other products. Competitors use vertical straps sewn into a garment that run from the upper shoulder or chest, down the back and terminating at the buttocks. The force of these straps are applied to the upper insertion points of the straps (which they call NeuroBands). The problem with these types of shirts is that the entire body has to be tight and if the wearer does not exactly fit the garment it is ineffective. The herein disclosed inner garment device extends along a length of the upper back. Specifically, the inner garment (PPR or IFG) device overlays a length of the rhomboids and upper trapezius and ends at about or above about the T-8 vertebrae of a wearer's spine. The PPR or IFG's benefit is that it applies diffused horizontal tension that mirrors the anatomy and the body of the garment can be loose or tight depending upon the user's preference.

The complete arc of movement that the shoulder joint is capable of resembles that of a "seesaw" motion. Medical terminology refers to this as the scapulohumeral rhythm and it can be thought of in two complimentary and overlapping steps. Initially the humerous is retracted in the posterior direction for the first 25-50% of the flexion, then the scapula.

Figure 8:
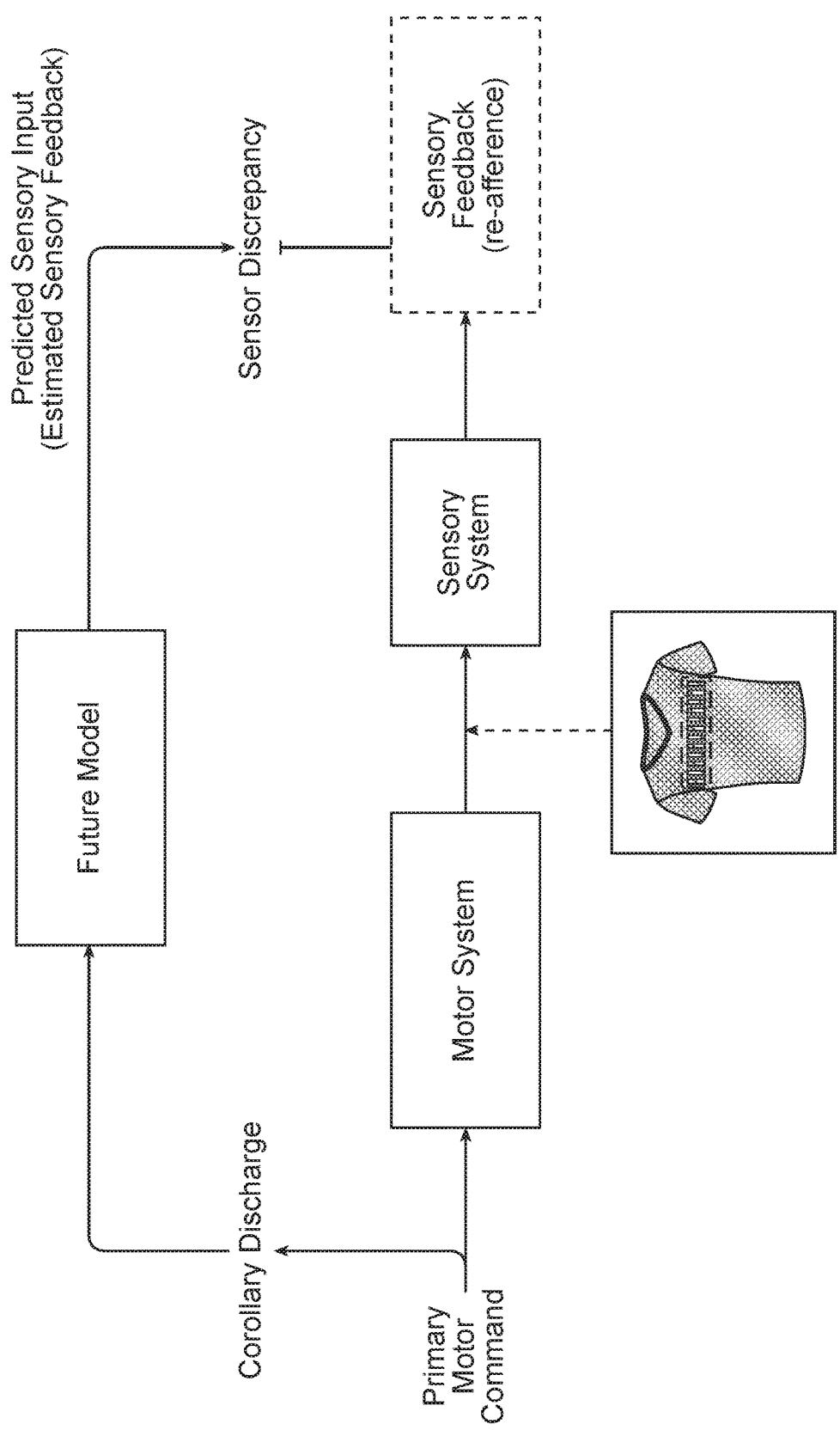
FIG. 8 is a flow diagram of the signal processes involved in proprioception and the targeted effect of the garment device.

FIG. 8 is a flow diagram of the signal processes involved in proprioception and the targeted effect of the garment device. The flow diagram is based on the corollary discharge model and can be used as a proprioceptive therapy prediction.

Figure 9:
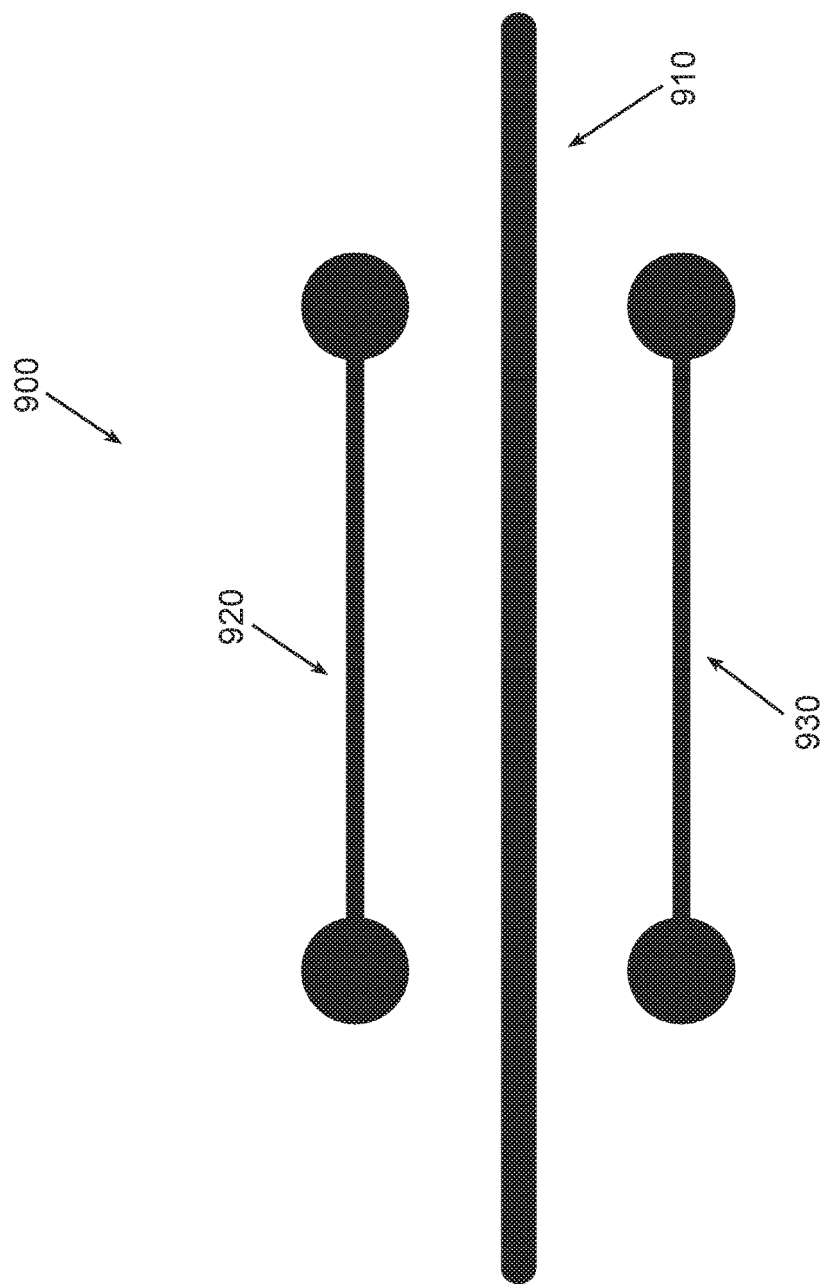
FIG. 9 is an embodiment of the casing material shown with the elastic strap and enveloping the elastic strap.

FIG. 9 is an embodiment of the casing material 920, and 930 shown with the elastic strap 910 and enveloping the elastic strap 910.

FIG. 10 shows the poly-elastic strap 1010, casing 1020 and four vertical seams 1030 according to an embodiment of the invention. FIG. 10 shows the vertical seams 1030 being evenly spaced throughout.

Having thus described several embodiments for practicing the inventive method, its advantages and objectives can be easily understood. Variations from the description above may and can be made by one skilled in the art without departing from the scope of the invention.

Accordingly, this invention is not to be limited by the embodiments as described, which are given by way of example only and not by way of limitation.

What is claimed is:

1. A wearable garment device for correcting a wearer's posture, the garment device comprising:
   a mesh anterior portion;
   a mesh posterior portion;
   a bottom edge defined along a bottom of said mesh anterior and mesh posterior portions;

said mesh anterior portion connected to said mesh posterior portion along first and second vertical seams;
a right sleeve;
a left sleeve;
said right sleeve connected to said mesh anterior portion and said mesh posterior portion along a right sleeve seam;
said left sleeve connected to said mesh anterior portion and said mesh posterior portion along a left sleeve seam; and
a single elastic strap extending horizontally from a lower portion of said right sleeve seam to a lower portion of said left sleeve seam along said mesh posterior portion and parallel to said bottom edge of the wearable garment device,
wherein, in use, said elastic strap is configured to extend along two scapulae of a wearer and across an upper posterior portion of the wearer's torso, and wherein said strap is configured to correct the wearer's posture by pulling the scapulae into postural alignment.

2. The garment device of claim 1, wherein the elastic strap is sewn into said mesh posterior portion.

3. The garment device of claim 1, further comprising a casing integrated into the elastic strap.

4. The garment device of claim 1, wherein the garment device corrects the wearer's posture by pulling the shoulders of the wearer to the posterior.

5. A wearable garment device for correcting a wearer's posture, the garment device comprising:
a mesh posterior portion;
a right sleeve;
a left sleeve;
a bottom edge defined along a bottom of said mesh posterior portion;
said right sleeve connected to said mesh posterior portion along a right sleeve seam;
said left sleeve connected to said mesh posterior portion along a left sleeve seam; and
an elastic strap extending horizontally from a lower portion of said right sleeve seam to a lower portion of said left sleeve seam along said mesh posterior portion and parallel to said bottom edge of the wearable garment device,
wherein, in use, said elastic strap is configured to extend along two scapulae of a wearer and across an upper posterior portion of the wearer's torso, and wherein said strap is configured to correct the wearer's posture by pulling the scapulae into postural alignment.

6. The garment device of claim 5, wherein the elastic strap is sewn into said mesh posterior portion.

7. The garment device of claim 5, further comprising a casing integrated into the elastic strap.

8. The garment device of claim 5, wherein the garment device corrects the wearer's posture by pulling the shoulders of the wearer to the posterior.

\* \* \* \* \*